(12) United States Patent
Liebsch

(10) Patent No.: US 9,316,585 B2
(45) Date of Patent: Apr. 19, 2016

(54) METHOD AND APPARATUS FOR DETERMINING A RELAXATION TIME DEPENDENT PARAMETER RELATED TO A SYSTEM

(71) Applicant: PreSens—Precision Sensing GmbH, Regensburg (DE)

(72) Inventor: Gregor Liebsch, Obertraubling (DE)

(73) Assignee: PreSens—Precision Sensing GmbH, Regensburg (DE)

(*) Notice: Subject to any disclaimer, the term of this patent is extended or adjusted under 35 U.S.C. 154(b) by 0 days.

(21) Appl. No.: 14/266,112

(22) Filed: Apr. 30, 2014

(65) Prior Publication Data

US 2014/0306125 A1    Oct. 16, 2014

Related U.S. Application Data

(63) Continuation of application No. PCT/EP2012/070552, filed on Oct. 17, 2012.

(60) Provisional application No. 61/558,530, filed on Nov. 11, 2011.

(30) Foreign Application Priority Data

Nov. 11, 2011  (DE) .......................... 10 2011 055 272

(51) Int. Cl.
*G01N 21/64*    (2006.01)

(52) U.S. Cl.
CPC .................................. *G01N 21/6408* (2013.01)

(58) Field of Classification Search
CPC  G01N 21/64; G01N 21/6408; G01N 21/6458
USPC .................................................... 250/459.1
See application file for complete search history.

(56) References Cited

U.S. PATENT DOCUMENTS

| 4,816,687 A | 3/1989 | Fehrenbach et al. |
| 5,102,625 A | 4/1992 | Milo |

(Continued)

FOREIGN PATENT DOCUMENTS

| DE | 3110943 | 9/1982 |
| DE | 3732216 | 4/1988 |

(Continued)

OTHER PUBLICATIONS

G. Liebsch; Klimant, B.; Frank, G. Holst; O.S. Wolfbeis: 'Luminescence, Lifetime Imaging of Oxygen, pH, and Carbon Dioxide Distribution Using Optical Sensors' Applied Spectroscopy Bd. 54, Nr. 4, 2000, Seiten 548-559.

(Continued)

*Primary Examiner* — Marcus Taningco
(74) *Attorney, Agent, or Firm* — Davidson, Davidson & Kappel, LLC

(57) ABSTRACT

A method for determining at least one parameter related to a system is disclosed, wherein the at least one parameter depends on at least one relaxation time of the system. The system is excited by a first series of electromagnetic excitation pulses, exhibiting a first defined time gap between consecutive excitation pulses. The response of the system to the first series of excitation pulses is integrated uninterruptedly over time, thus generating a first response signal. Likewise, by uninterrupted integration over time of at least one second response of the system, a second response-signal is generated. The at least one parameter is determined taking into account the first response-signal and the at least one second response-signal.

19 Claims, 6 Drawing Sheets

(56) References Cited

U.S. PATENT DOCUMENTS

| | | | |
|---|---|---|---|
| 5,304,809 A * | 4/1994 | Wickersheim | 250/458.1 |
| 5,315,993 A | 5/1994 | Alcala | |
| 6,081,127 A | 6/2000 | Wagner et al. | |
| 6,140,048 A | 10/2000 | Mueller | |
| 6,665,061 B1 * | 12/2003 | Abou-Saleh et al. | 356/73 |
| 2009/0146080 A1 | 6/2009 | Liebsch | |

FOREIGN PATENT DOCUMENTS

| | | |
|---|---|---|
| DE | 3732217 | 4/1988 |
| DE | 19511869 | 10/1996 |
| DE | 19634873 | 3/1998 |
| DE | 10152994 | 8/2003 |
| DE | 102005036410 | 2/2007 |
| DE | 102009013147 | 9/2010 |
| EP | 0442060 | 8/1991 |
| EP | 0927366 | 7/1999 |
| GB | 2113837 | 8/1983 |
| WO | WO03089889 | 10/2003 |

OTHER PUBLICATIONS

G. Liebsch; Klimant, C. Krause; O.S. Wolfbeis: 'Fluorescent imaging of pH with Optical Sensors Using Time Domain Dual Lifetime Referencing' Analytical Chemistry Bd. 73, Nr. 17, Sep. 1, 2001, Seiten 4354-4363.

* cited by examiner

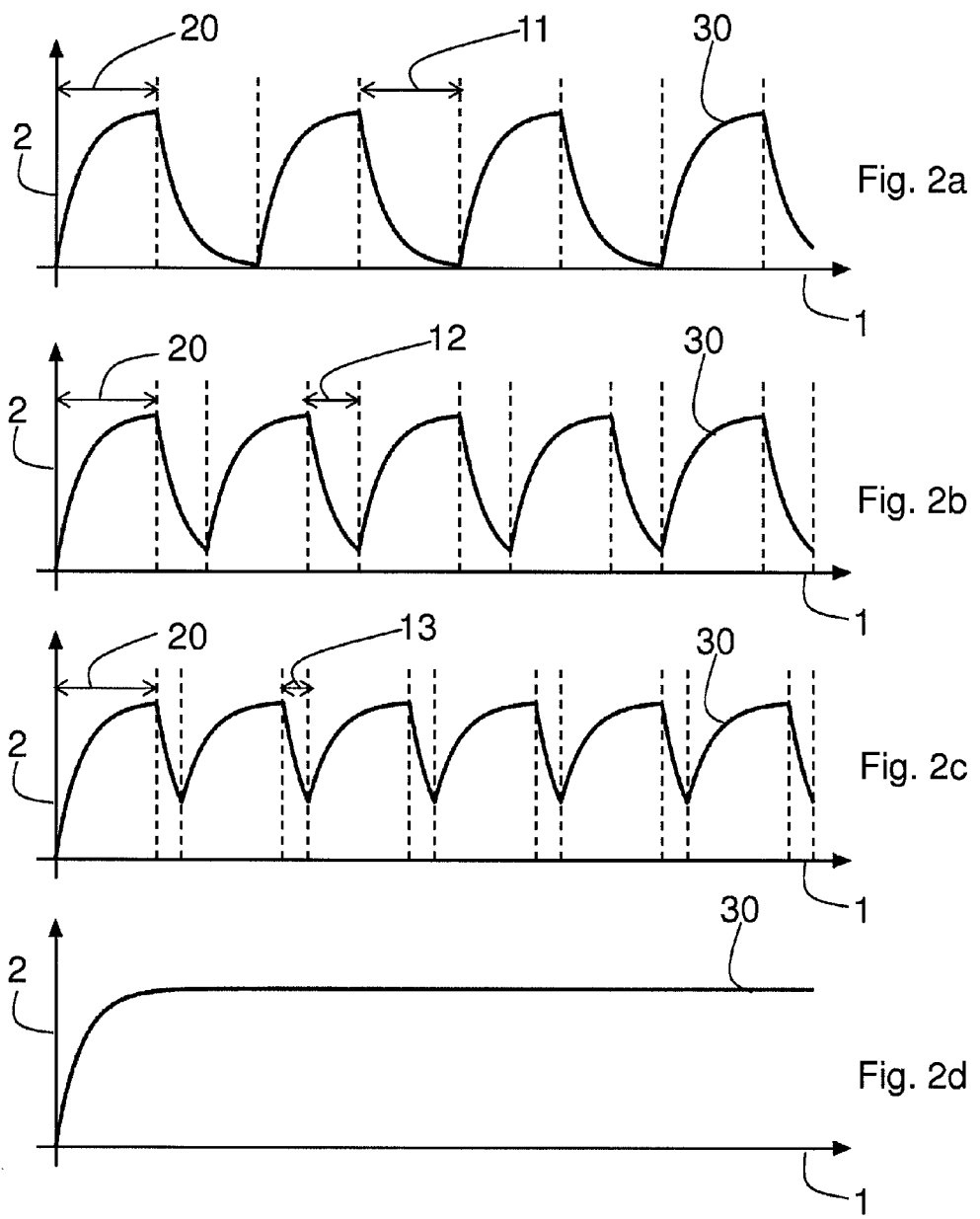

METHOD AND APPARATUS FOR DETERMINING A RELAXATION TIME DEPENDENT PARAMETER RELATED TO A SYSTEM

This is continuation application of International Patent Application PCT/EP2012/070552, filed Oct. 17, 2012, which claims the benefits of German Patent Application No. 10 2011 055 272.3, filed Nov. 11, 2011 and U.S. Provisional Patent Application No. 61/558,530, filed Nov. 11, 2011, all of which are incorporated by reference in their entireties herein.

The present invention relates to a method for determining at least one parameter related to a system, wherein the system exhibits at least one relaxation time and the at least one parameter depends on at least one relaxation time of the system.

Furthermore, the present invention relates to an apparatus for determining at least one parameter related to an object.

BACKGROUND

The German published patent application DE 196 34 873 A1 describes an apparatus and a method for distinguishing at least two types of molecule groups exhibiting different fluorescence, bound to analyte molecules, based on time-resolved fluorescence measurements. A light source for illuminating a sample volume is activated for a time interval $T_1$, then, after a time interval $T_2$ a detector is activated for a time $T_3$. From the variation in time of the detector signals recorded during the time interval $T_3$ it is determined which of the at least two molecule groups is contained in the sample volume.

The U.S. Pat. No. 5,315,993 discloses a probe and an apparatus for monitoring a plurality of parameters in an environment, making use of a luminescence phenomenon. A luminescence means is illuminated with a plurality of excitation light components, the amplitudes of which are modulated over time with set modulation frequencies. The luminescence response comprises a plurality of luminescence light components, which exhibit modulations corresponding to the modulations of the excitation light. Via a Fourier transform spectral data are obtained, which enter model equations, from which, inter alia, the lifetime of individual luminescence light components can be determined.

The German published patent application DE 101 52 994 A1 describes a method for the simultaneous optical determination of pH-value and dissolved oxygen of a predominantly aqueous sample. A single sensor matrix is used, containing at least two indicator dyes which produce at least one distinguishable optical signal for the measurable quantities pH-value and dissolved oxygen. In one disclosed embodiment of the method the pH-value and the dissolved oxygen are determined by measuring the decay time of a fluorescence response of the indicators to a pulse-shaped excitation.

The European patent application EP 0 442 060 A2 relates to a ratiometric luminescence measurement for determining a variable, for example the concentration of a substance. A first luminescent material with a first absorption band and a second luminescent material with a second absorption band are used; the first and the second absorption band do not overlap completely. In alternating first and second illumination intervals the luminescent materials are illuminated with a first excitation light within the first, but outside the second absorption band, and with a second excitation light within the second, but outside the first absorption band. The luminescence responses of the first and of the second luminescent material, correspondingly detected during respective first and second response intervals, are evaluated and are used for determining the variable.

The article "Luminescence Lifetime Imaging of Oxygen, pH, and Carbon Dioxide Distribution Using Optical Sensors" by G. Liebsch, I. Klimant, B. Frank, G. Hoist, and O. S. Wolfbeis in Applied Spectroscopy 54, No. 4 (2000), pages 548 to 559, describes the determination of various variables for samples in the wells of a microtiter plate via the dependence of the fluorescence lifetime of materials used as sensors on the respective variable. The fluorescence lifetime is determined as follows: the fluorescence is excited by a light pulse, after the end of which, during each of two intervals with a gap in between and preferentially of equal duration, the fluorescence response of the sensors is integrated. The fluorescence lifetime is determined from the quotient of the values of the integrals obtained in this way. In comparison with methods based on intensity only, this ratiometric method, based on a quotient of measured quantities, has the advantage of being practically independent of the local absolute values of the excitation energy.

The article "Fluorescent Imaging of pH with Optical Sensors Using Time Domain Dual Lifetime Referencing" by G. Liebsch, I. Klimant, C. Krause, and O. S. Wolfbeis in Analytical Chemistry Vol. 73, No. 17, Sep. 1, 2001, pages 4354 to 4363, relates to the determination of the pH-distribution in microtiter plates and on a surface. A combination of two luminescent materials, where the ratio of the amounts of the materials is fixed, is used: a fluorescent material, the fluorescence decay time of which depends on the pH-value, and a phosphorescent material, the phosphorescence decay-time of which is independent of the pH-value. The luminescent materials are excited by illumination, and during the excitation, within a first interval, the combined fluorescence and phosphorescence response of the materials is integrated. Immediately after the end of the excitation the recording of the luminescence response of the materials is interrupted for a period of time which is long enough for the fluorescence to decay practically completely. Afterwards, during a second time interval, which preferentially is of equal length as the first interval, the phosphorescence response of the phosphorescent material is integrated. From the quotient of the two values of the integrals eventually the pH-value can be inferred.

Luminescence-based measuring methods are known for the detection and the quantitative determination of many analytes. If the method is based on the intensity of the luminescence phenomenon, a reproducible illumination of the sample studied, in case of the illumination of an area for an extended sample also the spatial homogeneity of the illumination, is crucial. Other methods are based on the decay time of the luminescence phenomenon and exploit the fact that this decay time in case of numerous luminescent materials depends on specific variables of the environment; examples of such variables are pH-value, concentration of a substance, or temperature. With these methods, for which the prior art cited above contains examples, the luminescence response of a substance used as a sensor material is integrated over defined time intervals, and a ratio of the values of the integrals thus obtained is formed. By this formation of a quotient, due to which the methods are classified as ratiometric, the dependence on fluctuations of the illumination is considerably reduced. With these methods it is not necessarily the decay time or relaxation time of the luminescence phenomenon which is determined explicitly, but instead often a parameter which depends on the relaxation time, for example the quotient of the mentioned values of integrals. If a respective variable to be determined is calibrated against a corresponding respective parameter, the value of the variable can be found from the luminescence response. A difficulty with these methods, however, is to implement the defined time intervals for the integration of the luminescence response with sufficient precision in the measurement apparatus. This involves a certain technical effort implying corresponding costs. Furthermore the technology used is very sensitive, which makes its use, in particular for portable devices in the field, problematic, in particular again with respect to costs.

SUMMARY OF THE INVENTION

It is an object of the present invention to provide a method by which the determination of at least one parameter related to a system, wherein the parameter depends on at least one relaxation time of the system, is possible in a simple and cost-efficient way.

The present invention provides a method for determining at least one parameter related to a system, wherein the system exhibits at least one relaxation time, and the at least one parameter depends on the at least one relaxation time, the method comprises the following steps:
a) exciting the system by a first series of electromagnetic excitation pulses exhibiting a first defined time gap between consecutive excitation pulses;
b) determining a first response-signal by uninterrupted integration over time of a first response of the system to the first series of excitation pulses;
c) determining at least one second response-signal by uninterrupted integration over time of at least one second response of the system; and
d) determining the at least one parameter, taking into account therein the first response-signal and the at least one second response-signal.

A further an object of the invention is to provide a simple and cost-efficient apparatus, by which the determination of at least one parameter related to an object can be carried out wherein the parameter depends on at least one relaxation time of the object or system.

The object is achieved by an apparatus for determining at least one parameter related to an object, comprising:
  at least one sensor being associated with the object;
  a light source, being configured to emit light from different wavelength ranges, in order to excite the sensor to a luminescence required for the determination of a respective variable;
  a camera, wherein suitable filters are provided in a beam paths from the light source to the sensor, and from the sensor to the camera; and
  a control unit and an evaluation unit are connected with the camera and the light source.

In the method according to embodiments of the invention the system is excited by a first series of electromagnetic excitation pulses. Consecutive excitation pulses of the first series of excitation pulses therein exhibit a first defined time gap between them. The system reacts with a first response to the first series of excitation pulses, the first response is integrated uninterruptedly over time. The response of the system is detected with suitable detectors, for example a CCD chip, which may involve a signal conversion, for example from optical to electrical signals. Corresponding integration devices are also known to the skilled person. The integration of the first response of the system is done uninterruptedly, i.e. without interruption during the first series of excitation pulses, and therefore in particular is not restricted to specific defined time intervals within the duration of an excitation pulse or within a decay phase after an excitation pulse. Thus there is no technical effort to implement these defined time intervals for measurements. Therefore in particular detectors can be used for the method according to the embodiments of the invention which, in comparison with prior art methods where the integration is done over defined time intervals within a duration of a pulse and/or within the decay phase after an excitation pulse, react rather slowly and have rather a low sensitivity. Nonetheless the method yields useful results. This provides the opportunity for a considerable reduction of costs. The uninterrupted integration over time of the first response of the system provides a first response-signal.

In a different step of the method a second response-signal is obtained by uninterrupted integration over time of at least one second response of the system. Eventually, taking into account the first response-signal and the at least one second response-signal, the at least one parameter related to the system is determined. Determining here includes both the establishment of the at least one parameter up to error bounds typical in the art and of the method and only limiting the at least one parameter to a specific range. This specific range may be characterized by an upper bound and a lower bound, or by either an upper bound only or a lower bound only. In preferred embodiments determining the at least one parameter involves the formation of a quotient of the first response-signal and at least one second response-signal, so that the method is ratiometric, having the already mentioned advantage of reduction of the dependence on fluctuations of the illumination.

It is emphasized here that the characterization of a response of the system as first response or as second response does not imply a statement on the temporal order of the responses, the same applies to the first response-signal and the second response-signal, and likewise to the first series of excitation pulses and the second series of excitation pulses to be introduced below. In preferred embodiments the responses of the system are luminescence phenomena. Luminescence comprises at least fluorescence and phosphorescence.

In general, the at least one parameter which depends on at least one relaxation time may, for example, be the at least one relaxation time itself. However, it is also conceivable to use, for example, a quotient of two response-signals as a parameter to be determined; also a plurality of quotients of different response-signals may be determined, wherein each quotient is a parameter to be determined. Of course, other mathematical operations with the established response-signals may be conceived of for determining one or plural parameters related to the system.

In specific embodiments of the method at least one second response of the system is generated by exciting the system with a second series of electromagnetic excitation pulses. Consecutive excitation pulses of the second series of excitation pulses exhibit a second defined time gap between them, which is different from the first defined time gap between consecutive excitation pulses. In a variation of this embodiment, the system is excited by a plurality of second series of electromagnetic excitation pulses. For each second series of excitation pulses used, a respective second response-signal is determined. Each second series of excitation pulses exhibits a respective second defined time gap between consecutive excitation pulses, wherein at least two such second defined time gaps are different from each other.

In a preferred embodiment of the method at least one second response of the system is generated by exciting the system with a second series of electromagnetic excitation pulses. Consecutive excitation pulses of the second series of excitation pulses exhibit a second defined time gap between them which is different from the first defined time gap between consecutive excitation pulses. This embodiment is characterized in that first a threshold for the responses of the system is set. The first defined time gap between consecutive excitation pulses is chosen such that the first response of the system, which after an excitation pulse first is above the threshold, over time falls below the threshold within the chosen first defined time gap between consecutive excitation pulses. The second defined time gap between consecutive excitation pulses on the other hand is chosen such that a second response of the system, which after an excitation pulse first is above the threshold, does not fall below the threshold within the chosen second defined time gap between consecutive excitation pulses over time. Particularly preferred is to set the threshold for the responses of the system such that the threshold essentially corresponds to the specific noise of a measurement apparatus used for detecting the system responses, which means that a response of the system which falls below the threshold is compatible with zero within the precision of the measurement apparatus. Therefore in this case it can be said that a system the response of which to an excitation has eventually fallen below the threshold has fully relaxed for practical purposes.

In a further advantageous embodiment of the method the system is excited by a plurality of second series of electromagnetic excitation pulses. For each second series of excitation pulses used a respective second response-signal is determined. In this embodiment first a threshold for the responses of the system is set. The first defined time gap between consecutive excitation pulses is chosen such that the first response of the system falls below the threshold within the chosen first defined time gap between consecutive excitation pulses; the same remarks apply to choosing the threshold as for the embodiment described above. The second defined time gaps between consecutive excitation pulses for the successively employed second series of excitation pulses for the excitation of the system are obtained by stepwise reduction of the first defined time gap between consecutive excitation pulses.

In some embodiments of the method at least one second response of the system is a response of the system to a continuous excitation. This response and the corresponding second response-signal obtained therefrom by uninterrupted integration over time, are a reference value for the first response-signal and possible further second response-signals. The second response-signal for the continuous excitation can also be interpreted as response-signal for a zero time gap between excitation pulses.

In embodiments of the method at least one second response of the system is given by a further response of the system to the first series of excitation pulses. This for example may be the response of a luminescent substance to the first series of excitation pulses, wherein, for a respectively given measurement apparatus, the response of this luminescent substance only depends on the illumination, and thus allows to recognize temporal and/or spatial fluctuations of the illumination and to take these fluctuations into account for determining the at least one parameter, for example by removing the effects of such fluctuations from other responses of the system by calculations.

The frequency range of the electromagnetic radiation used for the excitation pulses is adapted to the respective measurement tasks, i.e. is chosen according to the frequency range required for exciting the desired response of the system. Usually the frequencies used are in a range from infrared light to the ultraviolet spectral range.

In advantageous embodiments of the method the system comprises an object and at least one sensor for capturing at least one variable of the object. Therein a respective at least one relaxation time of the at least one sensor, and thus a relaxation time of the system, depends on the at least one variable of the object. In this way, with these embodiments of the method, the value of the at least one variable of the object can be determined by determining the at least one parameter related to the system which depends on the at least one relaxation time. Therein a preceding calibration of the at least one parameter against the at least one variable may be required. It is not absolutely necessary to determine the at least one relaxation time explicitly in order to determine the at least one variable of the object. A variable of the object to be determined may for example be a concentration of a substance, a pressure, a partial pressure of a gas, a pH-value, or a temperature. Likewise any further variable can be determined for which suitable sensors are available which exhibit a relaxation time dependent on the respective variable to be determined. Numerous such sensors are known to the skilled person, examples thereof and of variables to be determined are to be found in the cited prior art.

Determining a variable of an object via the determination of a parameter dependent on a relaxation time according to the method according to embodiments of the invention can be used in many different ways. For example, studying one sample or an arrangement of a plurality of samples is possible; the one sample or the plurality of samples, respectively, therein corresponds to the object. For such a study, at least one sensor is assigned to each sample, and for each sample a respective first response-signal and a respective at least one second response-signal are determined. A specific embodiment thereof is a microtiter plate, wherein wells of the microtiter plate contain a respective sample and a respective at least one sensor. It is advantageous in particular for such arrangements to determine the first response-signal and the at least one second response-signal, respectively, simultaneously for a plurality of samples, by respectively exciting a plurality of samples simultaneously and recording the corresponding responses of the sensor simultaneously. For example, in case of a microtiter plate or a similar compact matrix-like arrangement of samples, a plurality of samples can be excited by an illumination spread over an area of the arrangement, such that a plurality of samples are within the illumination field, in particular the entire arrangement, for example the entire microtiter plate, may be illuminated.

In different embodiments of the method the at least one sensor is arranged on a surface of the object, in order to capture at least one variable on the surface of the object in a space-resolved manner. For this, the sensor may for example be arranged on a carrier film which is applied to the surface of the object. The method according to embodiments of the invention therein is carried out in a space-resolved embodiment. The responses of the system are captured in a space-resolved manner and are integrated over time uninterruptedly, so that space-resolved response-signals result, from which the at least one parameter is determined in a likewise space-resolved fashion. From the at least one parameter determined in a space-resolved fashion a distribution of the at least one variable on the surface of the object results. Here, too, a preceding calibration of the at least one parameter against the at least one variable may of course be necessary.

In particular embodiments of the method at least one sensor exhibits at least one inert relaxation time, i.e. a relaxation time which does not depend on the at least one variable of the object. A response-signal corresponding to a response with this relaxation time may be used as a reference for the illumination. This is particularly advantageous for the above-described space-resolved embodiment of the method, as in this way inhomogeneities of the illumination may be recognized and taken into account for determining the at least one parameter from the response-signals. For embodiments in which the responses of the system are given by luminescence phenomena it is particularly advantageous, if the response of the system which corresponds to the inert relaxation time is in a spectral range which is different from the spectral range in which those responses of the system are situated the relaxation time of which does depend on a variable of the system.

In particular embodiments, using a sensor with at least one inert relaxation time, also inhomogeneities within the sensor can be recognized and compensated in the evaluation. If for example a sensor is used the response of which is a luminescence phenomenon, the intensity of the luminescence at a specific spot of the sensor not only depends on the illumination and possible variables of the object, but also on the concentration of a luminescent substance or of luminescent particles at the specific spot of the sensor. In order to counter inhomogeneities in the distribution of the luminescent substance or of the luminescent particles, substances or particles may be used which exhibit at least two different luminescence phenomena. One luminescence phenomenon which has a relaxation time dependent on at least one variable of the object, and one luminescence phenomenon which has an inert relaxation time. In this way the concentration of the luminescent substance or of the luminescent particles at a specific spot of the sensor can be taken into account by including the luminescence phenomenon with the inert relaxation time in the determination of the at least one parameter.

A general advantage of a pulsed excitation should be mentioned here which is not limited to the method according to the invention: As during the time gaps between consecutive excitation pulses the system is not exposed to electromagnetic excitation radiation, a heightened contrast results for the response of the system, and thus an improved precision of the detection of the response of the system, and ultimately an improved precision, for example, for determining the at least one variable.

BRIEF DESCRIPTION OF THE DRAWINGS

Below embodiments of the method according to the invention are illustrated further with reference to the accompanying figures.

FIG. 2a shows a response of the system to a series of excitation pulses with a first defined time gap between consecutive excitation pulses over time.

FIG. 2b shows a response of the system to a series of excitation pulses with a second defined time gap between consecutive excitation pulses over time.

FIG. 2c shows a response of the system to a series of excitation pulses with a further second defined time gap between consecutive excitation pulses over time.

FIG. 2d shows a response of the system to a continuous excitation.

DETAILED DESCRIPTION

Figure 1A:
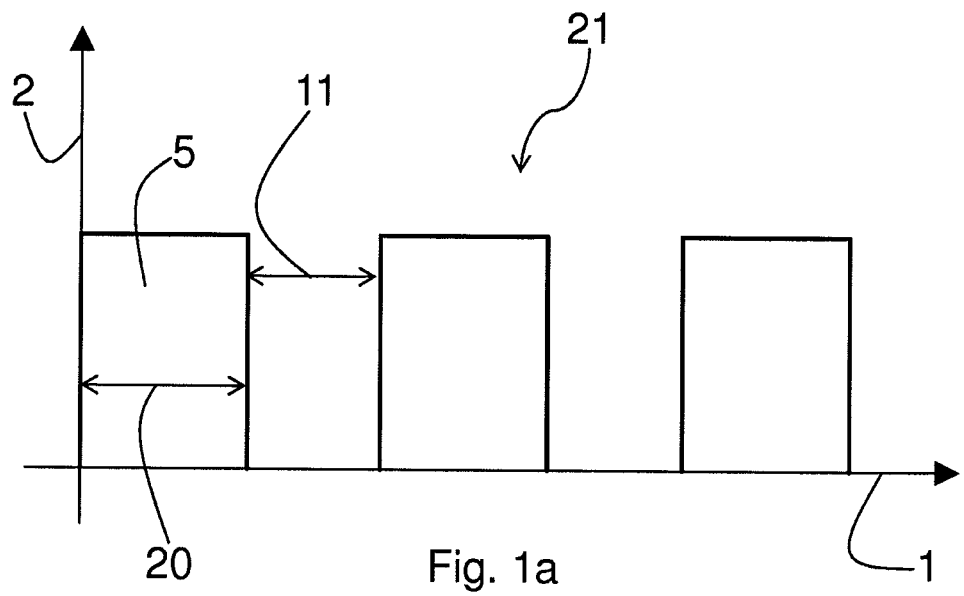
FIG. 1a shows a first series of excitation pulses with a first defined time gap between consecutive excitation pulses.

In the figures like reference numerals are used for like elements or elements of like function. Furthermore, for the sake of clarity, only those reference numerals are shown in the figures which are necessary for discussing the respective figure.

FIG. 1a shows a first series 21 of excitation pulses 5. Time is shown on the abscissa 1, the strength of the excitation pulses 5 is shown on the ordinate 2. The excitation pulses 5 have a respective pulse duration 20. In the first series 21 of excitation pulses 5 consecutive excitation pulses 5 have a first defined time gap 11 between them.

Figure 1B:
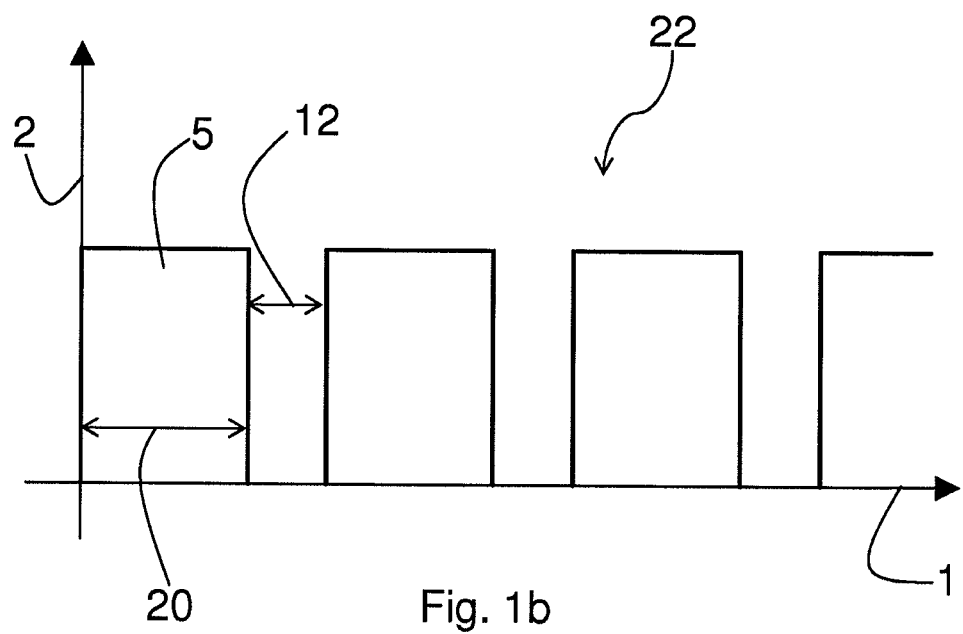
FIG. 1b shows a second series of excitation pulses with a second defined time gap between consecutive excitation pulses.

FIG. 1b shows a second series 22 of excitation pulses 5. Time is shown on the abscissa 1, the strength of the excitation pulses 5 is shown on the ordinate 2. The excitation pulses 5 have a respective pulse duration 20. In the second series 22 of excitation pulses 5 consecutive excitation pulses 5 have a second defined time gap 12 between them, which in this figure is smaller than the first defined time gap 11 shown in FIG. 1a.

In FIGS. 1a and 1b the excitation pulses 5 are of rectangular shape. This, however, is just one possible pulse shape and is not to be considered a limitation of the invention; the skilled person knows that different pulse shapes exist, and it is apparent to the skilled person that the method according to the invention can also be carried out with pulse shapes different from rectangular pulses.

FIG. 2a schematically shows, in dependence on time, a response 30 of a system to a series of excitation pulses 5 (see FIGS. 1a and 1b) with a first defined time gap 11 between consecutive excitation pulses. The time is shown on the abscissa 1, on the ordinate 2 a value is shown which characterizes the strength of the response 30 of the system; in case the response 30 of the system is a luminescence phenomenon, such a value is given for example by the intensity of the luminescence radiation, or by an electrical signal generated therefrom by a detector, like a CCD-Chip of a camera 113 (see FIGS. 5 and 6). In FIG. 2a it is shown that during the duration 20 of a respective excitation pulse 5 the response 30 of the system grows, whereas during the first defined time gap 11 between consecutive excitation pulses the response 30 of the system respectively drops. This drop is determined by at least one relaxation time of the response 30 of the system; it is evident to the skilled person that in this context relaxation time of the response of the system is used synonymously with relaxation time of the system.

FIG. 2b is analogous to FIG. 2a, but schematically shows, in dependence on time, the response 30 of the system to a series of excitation pulses 5 (see FIGS. 1a and 1b) with a second defined time gap 12 between consecutive excitation pulses. The second defined time gap 12 between consecutive excitation pulses here is shorter than the first defined time gap 11 between consecutive excitation pulses in FIG. 2a. The pulse duration 20 of an excitation pulse 5 and the relaxation time of the response 30 of the system have the same values as in FIG. 2a.

FIG. 2c is analogous to FIG. 2a, but schematically shows, in dependence on time, the response 30 of a system to a series of excitation pulses 5 (see FIG. 1) with a further second defined time gap 13 between consecutive excitation pulses. The further second defined time gap 13 between consecutive excitation pulses here is shorter than the second defined time gap 12 in FIG. 2b, and here thus of course also shorter than the first defined time gap 11 in FIG. 2a. The pulse duration 20 of an excitation pulse 5 as well as the relaxation time of the response 30 of the system have the same values as in FIG. 2a.

In FIGS. 2a, 2b, and 2c it is evident that a shorter defined time gap 11, 12, 13 between consecutive excitation pulses, all other conditions being equal, results in the respective local minima of the respective response 30 of the system having higher values of the response 30 of the system, and in a higher average value of the response 30 of the system. This means that on integration of the response 30 of the system over a defined time interval which extends over a plurality of pulse durations 20 and of defined time gaps 11, 12, 13 between consecutive excitation pulses the value of the resulting integral in the case of FIG. 2c is higher than in the case of FIG. 2b, and in turn in the case of FIG. 2b is higher than in the case of FIG. 2a. The longer the defined time interval for the integration, the larger, and thus the more pronounced, the differences between the values of the integrals become. In this way an increased resolution of the method with respect to the relaxation time results through the integration, and it is also possible to capture and distinguish an increased range of relaxation times. Larger differences between the values of the integrals imply larger differences between the response-signals and thus a more reliable determination of at least one parameter which depends on at least one relaxation time. As the integration is done uninterruptedly over a plurality of pulse durations 20 and of defined time gaps 11, 12, 13 between consecutive excitation pulses, using a detector exhibiting reaction times considerably below the pulse duration 20 or the defined time gaps 11, 12, 13 between consecutive excitation pulses is not necessary for recording the respective response of the system. Such a detector, however, would be necessary for prior art methods in which the integration is restricted to time intervals within the duration of an excitation pulse and/or within a time gap between consecutive excitation pulses.

FIG. 2d is analogous to FIG. 2a, but schematically shows, in dependence on time, the response 30 of the system to a continuous excitation. The relaxation time of the response of the system has the same value as in the cases of FIGS. 2a, 2b, and 2c. If the response 30 of the system to the continuous excitation is integrated over a predefined time interval, in comparison with the cases of FIGS. 2a, 2b, and 2c, all other conditions being equal, a maximum value of the corresponding integrals of the respective response 30 over an identical predefined time interval results.

Figure 3:
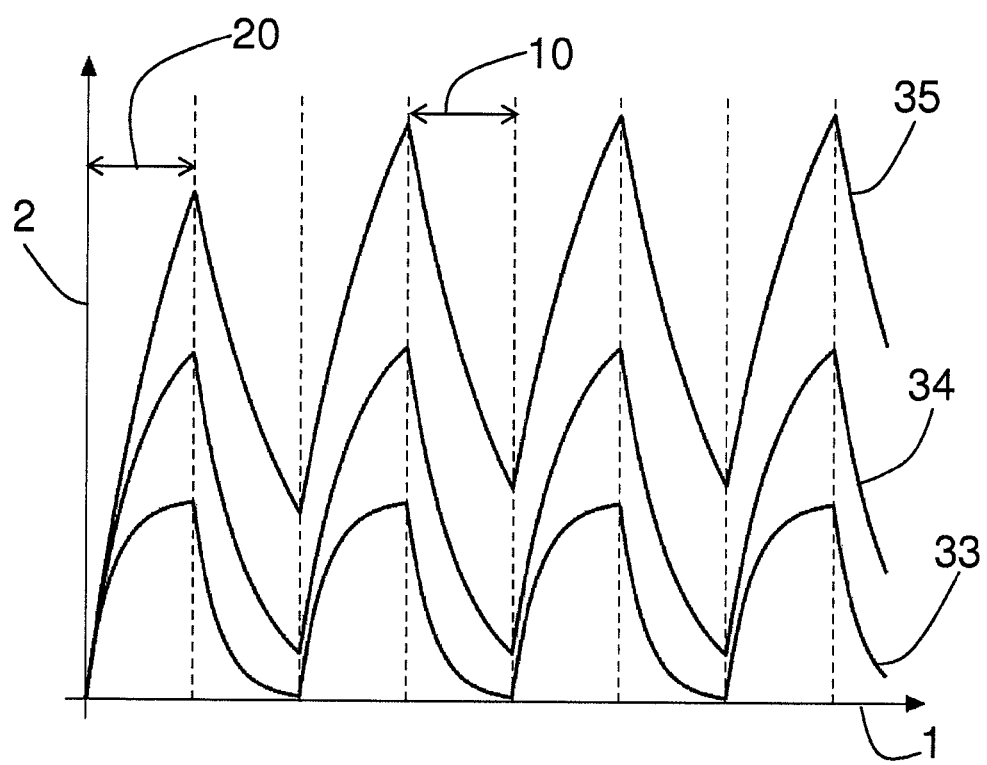
FIG. 3 shows responses of the system to a series of excitation pulses for different relaxation times of the system over time.

In FIG. 3 the time is shown on the abscissa 1, and on the ordinate 2 a value characterizing the strength of the response of the system is shown, as in the case of FIGS. 2a, 2b, 2c, 2d. Shown in schematic representation are responses 33, 34, 35 of the system to a series of excitation pulses 5 (see FIGS. 1a and 1b) with pulse duration 20 and a defined time gap 10 between consecutive excitation pulses, wherein the responses 33, 34, 35 of the system exhibit different relaxation times. During the duration 20 of an excitation pulse 5 the response 33, 34, 35, respectively, of the system grows, whereas the response 33, 34, 35, respectively, of the system drops during the defined time gap 10 between consecutive excitation pulses. The drop is determined by the respective relaxation time; therein, in the case of the response 33 of the system, the relaxation time is shorter than the relaxation time in the case of the response 34 of the system, and this in turn is shorter than in the case of response 35 of the system.

It is evident that with increasing relaxation time a higher value of the respective response 33, 34, 35 of the system results over time. Therefore, on integration of the respective response 33, 34, 35 of the system over a defined time interval, a value results which is the higher the longer the relaxation time is. The longer the defined time interval, the larger, and thus the more pronounced, the differences between the values of the integrals become. In this way an increased resolution of the method according to embodiments of the invention with respect to the relaxation time results through the integration, and it is also possible to capture and distinguish an increased range of relaxation times. Larger differences between the values of the integrals imply larger differences between the response-signals, and thus a more reliable and more precise determination of at least one parameter which depends on at least one relaxation time.

Figure 4A:
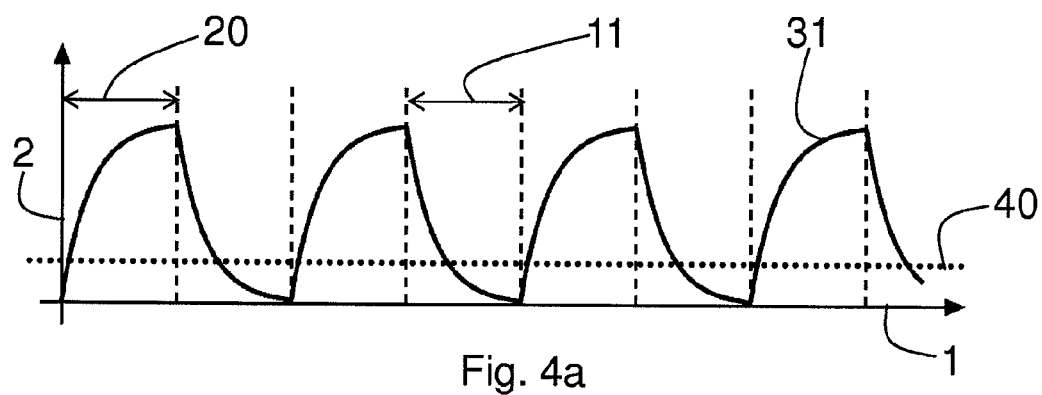
FIG. 4a shows a first response of the system to a first series of excitation pulses over time, with a first defined time gap between consecutive excitation pulses, in relation to a threshold.

FIG. 4a shows, in dependence on time, a first response 31 of the system 105 (see FIGS. 5 and 6) to a first series 21 (see FIG. 1a) of excitation pulses 5 (see FIGS. 1a and 1b) with a first defined time gap 11 between consecutive excitation pulses. The time is shown on the abscissa 1, on the ordinate 2 is shown a value which represents the strength of the first response 31 of the system 105. Furthermore a threshold 40 is shown.

Figure 4B:
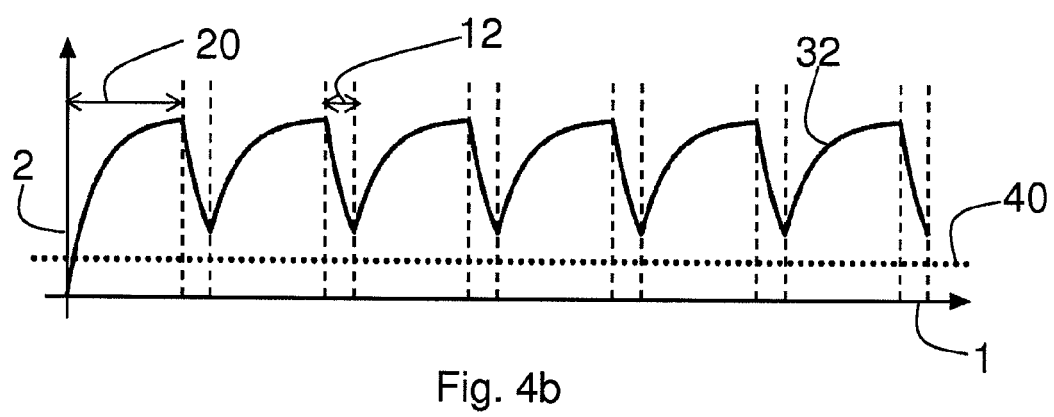
FIG. 4b shows a second response of the system to a second series of excitation pulses over time, with a second defined time gap between consecutive excitation pulses, in relation to a threshold.

FIG. 4b shows, in dependence on time, a second response 32 of the system 105 (see FIGS. 5 and 6) to a second series 22 (see FIG. 1b) of excitation pulses 5 (see FIGS. 1a and 1b) with a second defined time gap 12 between consecutive excitation pulses. The time is shown on the abscissa 1, on the ordinate 2 is shown a value which represents the strength of the second response 32 of the system 105. Furthermore a threshold 40 is shown.

The threshold 40 in the case of FIG. 4a has the same value as in the case of FIG. 4b and is chosen such that the first response 31 of the system 105 and the second response 32 of the system 105, respectively, first are above the threshold 40 after an excitation pulse 5.

The first defined time gap 11 between consecutive excitation pulses in the case of FIG. 4a is chosen such that the first response 31 falls below the threshold 40 during the first defined time gap 11 between consecutive excitation pulses. The second defined time gap 12 is chosen such that the second response 32 does not fall below the threshold 40 during the second defined time gap 12 between consecutive excitation pulses. The second defined time gap 12 between consecutive excitation pulses herein is shorter than the first defined time gap 11 between consecutive excitation pulses.

Preferentially the threshold 40 is chosen such that falling below the threshold 40 is compatible with a value zero of the first response 11 or of the second response 12, respectively, of the system 105 within the precision of the measurement apparatus 100 (see FIGS. 5 and 6). Falling below the threshold 40 then is practically equal to a complete relaxation of the system 105 after one or plural excitation pulses 5.

Figure 5:
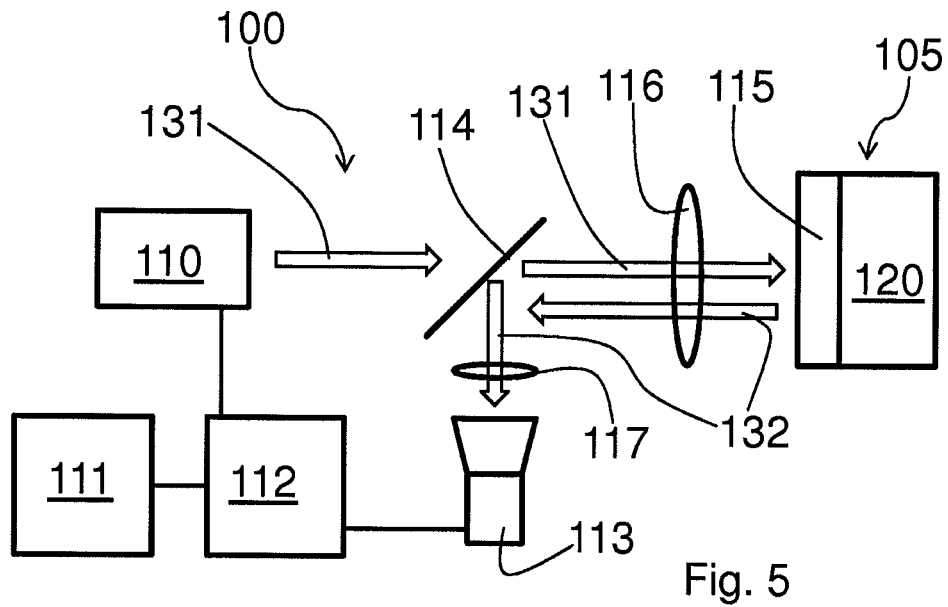
FIG. 5 schematically shows a possible apparatus for carrying out the method according to the invention.

FIG. 5 shows the schematic configuration of a possible measurement apparatus 100 with which the method according to the invention can be carried out. It is apparent to the skilled person that the method according to the invention can also be carried out with different technical means and that it is not restricted to the apparatus shown. In the embodiment shown the system 105 for which at least one parameter is to be determined comprises an object 120 and a sensor 115. The sensor 115 therein exhibits at least one relaxation time which depends on a variable of the object 120. A light source 110 emits excitation light, indicated by arrows 131, for exciting a luminescence phenomenon in the sensor 115, which in the embodiment shown here is a layer applied on the object 120. In the embodiment shown the luminescence light emitted from sensor 115 and indicated by arrows 132 has a wavelength different from the excitation light, and is directed to a camera 113 by a dichroic beam splitter 114. The camera 113 is connected with an evaluation unit 111. Camera 113, light source 110 and evaluation unit 111 are controlled by a control unit 112. As indicated in the figure, further optical elements 116, 117 may be present.

A task of the control unit 112 is, amongst others, to cause the light source 110 to emit excitation pulses 5 (see FIGS. 1a and 1b) as light pulses of defined pulse duration 20 (see FIGS. 1a and 1b) and with a defined time gap 10, 11, 12, 13 (see FIGS. 1a, 1b, 2a, 2b, 2c, 3) between consecutive excitation pulses 5. At the start of the emission of a series of excitation pulses 5 by the light source 110, the control unit 112 also causes the start of the integration over time of the response of the system 105, i.e. here of the sensor 115, in the form of luminescence light, recorded by the camera 113. The control unit 112 further allows to set the number of pulses in a series of excitation pulses 5 as well as to specify a number of repetitions of a measurement, for example in order to improve the signal-to-noise ratio or to determine the variation in time of a variable of the object 120. The control unit 112 also allows specifying the respective pulse durations 20 and respective defined time gaps 10, 11, 12, 13 between consecutive excitation pulses to be used with a sequence of series of excitation pulses 5, and generally to select the sequence of excitations to be used, i.e. series of excitation pulses 5 or continuous excitation. Likewise, a value for the intensity of the illumination light can be set.

The evaluation unit 111 determines the first and second response-signals by uninterrupted time integration of the respective responses of the system 105 over a time interval to be specified by the control unit 112, determines the at least one parameter related to the system 105 therefrom, and therefrom the at least one variable of the object. In case of a sensor 115 extended over an area, as shown in FIG. 5, this can be done in a space-resolved manner.

Of course the measurement apparatus 100 may also be configured to determine a plurality of variables of the object 120, wherein each variable is determined according to the method according to embodiments of the invention. For this purpose the light source 110 may be configured to emit light from different wavelength ranges, in order to excite the sensor 115 to a luminescence required for the determination of a respective variable. It is apparent to the skilled person that therein suitable filters may be provided in the beam paths from the light source 110 to the sensor 115, and from the sensor 115 to the camera 113. It is also evident to the skilled person that in specific embodiments of the measurement apparatus 100, with filters in particular in front of the camera 113, an ordinary beam splitter can be used instead of the dichroic beam splitter 114.

Figure 6:
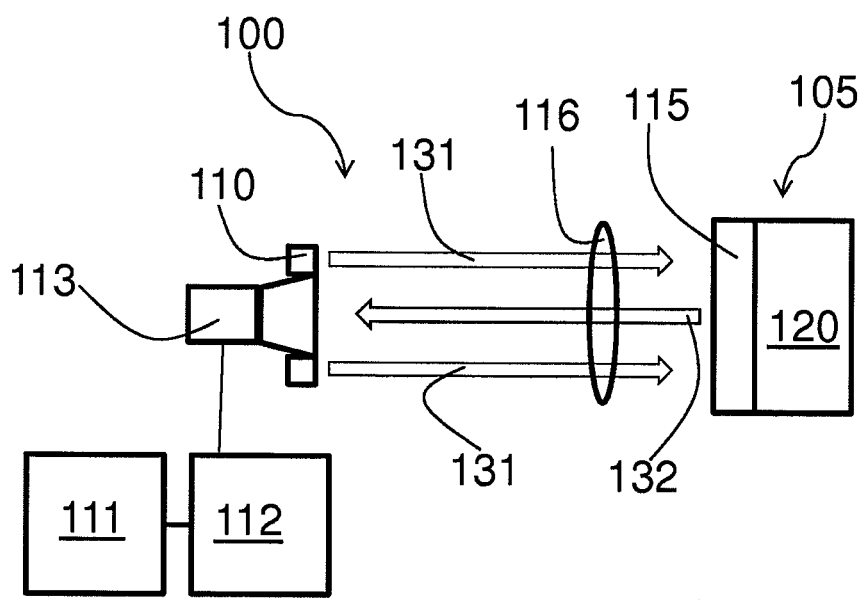
FIG. 6 schematically shows a further possible apparatus for carrying out the method according to the invention.

FIG. 6 shows the schematic configuration of a further possible measurement apparatus 100 with which the method according to the invention can be carried out. All essential elements have already been described and discussed in the context of FIG. 5. In this embodiment the light source 110 is a ring-light around the objective of the camera 113. The excitation light emitted by the light source 110 is indicated by arrows 131, luminescence light emitted by the sensor 115 is indicated by the arrow 132. Here, too, further optical elements 116 may be present in the beam path. In particular it is possible to adapt the light from the light source to measurement tasks by filters, and/or to provide filters for the luminescence light emitted from the system 105 in front of the objective of the camera 113.

In the context of the FIGS. 5 and 6 it is apparent to the skilled person that the excitation light and the luminescence light can propagate through vacuum or a medium, for example air, a different gas or gas mixture, or a liquid. It is also possible to pass excitation light and/or luminescence light through waveguides.

Instead of the camera, according to the measurement task, any other light detection device can be used by which the luminescence light can be detected and converted for the evaluation according to the invention, for example a photodetector. For a space-resolved variant of the method space-resolved recording of the sensor responses is required; a camera, for example, is particularly suited for this. If space-resolved capturing is not required, for example a photocell may be used.

Figure 7:
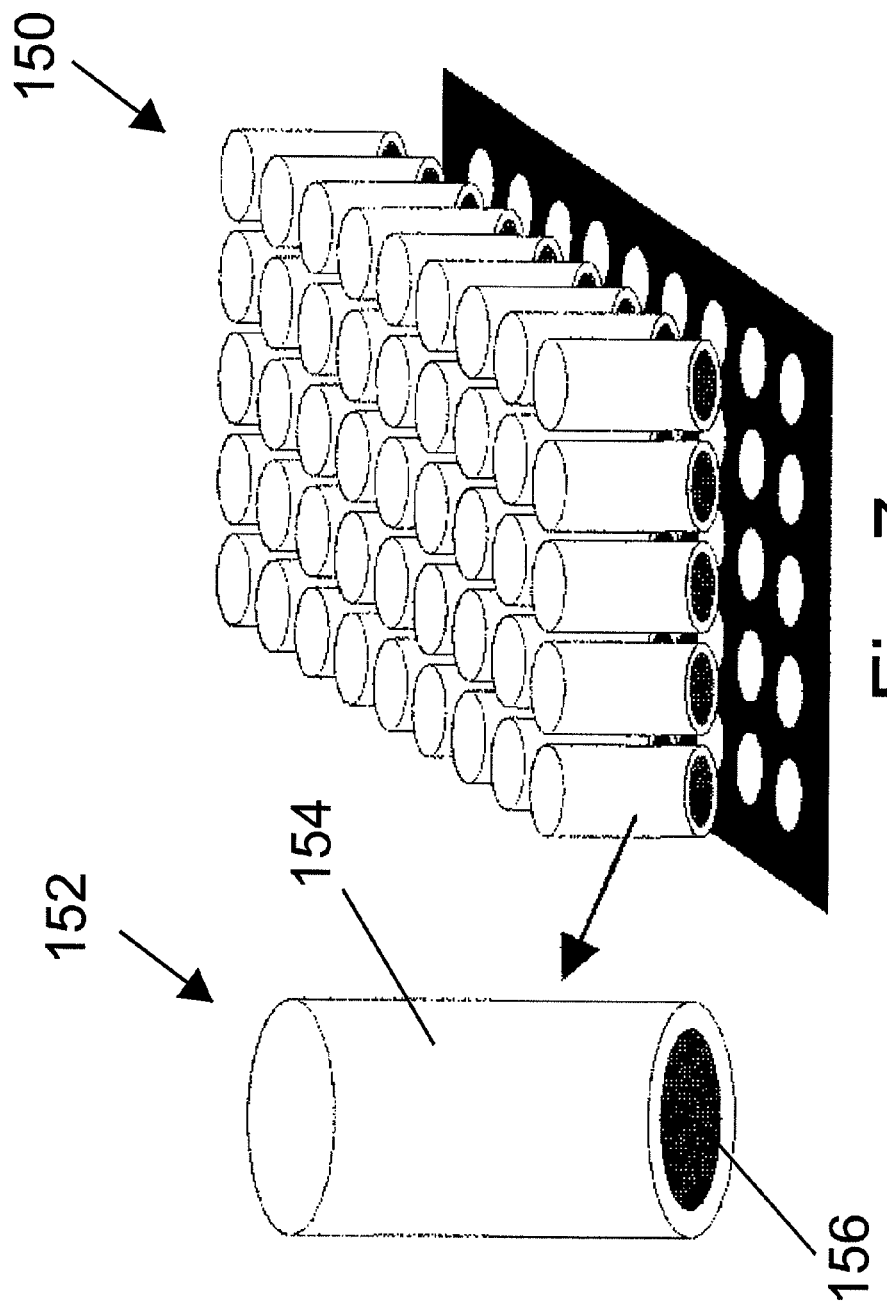
FIG. 7 schematically shows a microtiter plate having wells containing a respective sample and a respective at least one sensor.

Determining a variable of an object via the determination of a parameter dependent on a relaxation time according to the method according to embodiments of the invention can be used in many different ways. For example, studying one sample or an arrangement of a plurality of samples is possible; the one sample or the plurality of samples, respectively, therein corresponds to the object. For such a study, at least one sensor is assigned to each sample, and for each sample a respective first response-signal and a respective at least one second response-signal are determined. FIG. 7 shows a specific embodiment thereof illustrating a microtiter plate 150, wherein wells 152 of the microtiter plate 150 contain a respective sample 154 and a respective at least one sensor 156. It is advantageous in particular for such arrangements to determine the first response-signal and the at least one second response-signal, respectively, simultaneously for a plurality of samples 154, by respectively exciting a plurality of samples 154 simultaneously and recording the corresponding responses of the sensor 156 simultaneously. For example, in case of a microtiter plate 150 or a similar compact matrix-like arrangement of samples, a plurality of samples can be excited by an illumination spread over an area of the arrangement, such that a plurality of samples are within the illumination field, in particular the entire arrangement, for example the entire microtiter plate 150, may be illuminated.

The invention has been described with reference to preferred embodiments. It is, however, known to the skilled person that alterations and modifications are possible without leaving the scope of the subsequent claims.

What is claimed is:

1. A method for determining at least one parameter related to a system, the system exhibiting at least one relaxation time, the at least one parameter depending on the at least one relaxation time, the method comprising:

exciting the system by a first series of electromagnetic excitation pulses exhibiting a first defined time gap between consecutive excitation pulses;

determining a first response-signal by uninterrupted integration over time of a first response of the system to the first series of excitation pulses, the integration being done uninterruptedly over a plurality of pulse durations of the excitation pulses and defined time gaps between consecutive excitation pulses;

determining at least one second response-signal by uninterrupted integration over time of at least one second response of the system; and determining the at least one parameter, taking into account therein the first response-signal and the at least one second response-signal.

2. The method as recited in claim 1 wherein the at least one second response of the system is generated by a second series of electromagnetic excitation pulses exhibiting a second defined time gap between consecutive excitation pulses, the second defined time gap being different from the first defined time gap.

3. The method as recited in claim 2 wherein the second series of electromagnetic excitation pulses includes a plurality of second series of electromagnetic excitation pulses exciting the system, and the at least one second response signal includes a respective second response-signal is determined for each second series of excitation pulses, wherein each second series of excitation pulses exhibits a second defined time gap between consecutive excitation pulses, at least two such second defined time gaps between consecutive excitation pulses being different from each other.

4. The method as recited in claim 3 further comprising:
setting a threshold for the responses of the system;
selecting the first defined time gap between consecutive excitation pulses such that the first response of the system falls below the threshold within the selected first defined time gap between consecutive excitation pulses;
selecting the successively employed second defined time gaps between consecutive excitation pulses by stepwise reduction of the first defined time gap between consecutive excitation pulses.

5. The method as recited in claim 2 further comprising:
setting a threshold for the responses of the system;
selecting the first defined time gap between consecutive excitation pulses such that the first response of the system falls below the threshold within the selected first defined time gap between consecutive excitation pulses; and
selecting the second defined time gap between consecutive excitation pulses such that the second response of the system does not fall below the threshold within the selected second defined time gap between consecutive excitation pulses.

6. The method as recited in claim 1 wherein the at least one second response of the system is a response of the system to a continuous excitation.

7. The method as recited in claim 1 wherein the at least one second response of the system is a further response of the system to the first series of excitation pulses.

8. The method as recited in claim 1 wherein the determining the at least one parameter includes forming a ratio between the first response-signal and at least one second response-signal.

9. The method as recited in claim 1 wherein the system is excited by light.

10. The method as recited in claim 1 wherein the first response of the system and the at least one second response of the system are fluorescence, phosphorescence, or luminescence phenomena.

11. The method as recited in claim 1 wherein the system comprises an object and at least one sensor for capturing at least one variable of the object, a respective at least one relaxation time of the at least one sensor depending on the at least one variable of the object.

12. The method as recited in claim 11 wherein the at least one variable of the object is a concentration of a substance, a pressure, a partial pressure of a gas, a pH value, or a temperature.

13. The method as recited in claim 11 wherein the object is an arrangement of at least two samples, a respective at least one sensor corresponds to each sample, and for each sample a respective first response-signal and a respective at least one second response-signal are determined.

14. The method as recited in claim 13 wherein each of a plurality of wells of a microtiter plate contains one of the samples and at least one of the sensors.

15. The method as recited in claim 13 wherein the first response-signal and the at least one second response-signal, respectively, are determined simultaneously for a plurality of the samples.

16. The method as recited in claim 11 wherein the at least one sensor is arranged on a surface of the object, the responses of the system are recorded uninterruptedly over time in a space-resolved manner, the response-signals are correspondingly determined in a space-resolved manner, the at least one parameter is determined in dependence on spatial location, and a distribution of the at least one variable on the surface of the object is correspondingly determined in dependence on spatial location.

17. The method as recited in claim 11 wherein the at least one sensor exhibits a relaxation time which does not depend on the at least one variable of the object.

18. A method for determining at least one parameter related to a system, the system exhibiting at least one relaxation time, the at least one parameter depending on the at least one relaxation time, the method comprising:
exciting the system by a first series of electromagnetic excitation pulses exhibiting a first defined time gap between consecutive excitation pulses;
determining a first response-signal by uninterrupted integration over time of a first response of the system to the first series of excitation pulses, a threshold for the first response of the system being set, the integration being done uninterruptedly over a plurality of pulse durations of the excitation pulses and defined time gaps between consecutive excitation pulses;
selecting the first defined time gap between consecutive excitation pulses such that the first response of the system falls below the threshold within the selected first defined time gap between consecutive excitation pulses;
determining at least one second response-signal by uninterrupted integration over time of at least one second response of the system, a threshold for the second response of the system being set; and
determining the at least one parameter, taking into account therein the first response-signal and the at least one second response-signal.

19. An apparatus for determining at least one parameter related to an object, comprising:
at least one sensor associated with the object;
a light source configured to emit light from different wavelength ranges, in order to excite the at least one sensor to a luminescence required for the determination of a respective variable;
a camera, suitable filters being provided in a beam paths from the light source to the sensor, and from the sensor to the camera; and
a control unit and an evaluation unit connected with the camera and the light source,
the control unit configured for causing the light source to excite the at least one sensor by emitting a first series of electromagnetic excitation pulses exhibiting a first defined time gap between consecutive excitation pulses, the evaluation unit configured for determining a first response-signal by uninterrupted integration over time of a first response of the system to the first series of excitation pulses, the integration being done uninterruptedly over a plurality of pulse durations of the excitation pulses and defined time gaps between consecutive excitation pulses.

* * * * *